(12) United States Patent
MacKool

(10) Patent No.: US 6,875,194 B2
(45) Date of Patent: Apr. 5, 2005

(54) REDUCTION OR ELIMINATION OF THE INTRODUCTION OF AIR WITHIN FLUID INTRODUCED INTO A SURGICAL FIELD

(75) Inventor: Richard J. MacKool, Astoria, NY (US)

(73) Assignee: Alcon, Inc., Hünenberg (CH)

( * ) Notice: Subject to any disclaimer, the term of this patent is extended or adjusted under 35 U.S.C. 154(b) by 162 days.

(21) Appl. No.: 10/373,518

(22) Filed: Feb. 25, 2003

(65) Prior Publication Data

US 2004/0167462 A1 Aug. 26, 2004

(51) Int. Cl.[7] ............................................. A61M 1/00
(52) U.S. Cl. ........................ 604/28; 604/27; 604/122; 73/865.9; 73/37
(58) Field of Search .......................... 604/27–28, 30, 604/35, 43, 45, 93.01, 122–123, 125; 606/107; 73/865.9, 37, 37.5–37.9, 46, 49.1, 49.5, 49.8

(56) References Cited

U.S. PATENT DOCUMENTS

| 5,213,569 A | * | 5/1993 | Davis ......................... 604/22 |
| 2004/0089080 A1 | * | 5/2004 | Kadziauskas et al. ...... 73/865.9 |

* cited by examiner

*Primary Examiner*—Nicholas D. Lucchesi
*Assistant Examiner*—Catherine S. Williams
(74) *Attorney, Agent, or Firm*—Gibbons, Del Deo, Dolan, Griffinger & Vecchione

(57) ABSTRACT

Air bubbles can be reduced or eliminated from the infusion source used during surgical procedures which require the delivery of irrigating fluid to the operating field. This is particularly a problem during surgical procedures performed within a closed organ, such as the eye. A constant low rate of infusion is created upon removal of a test chamber from a surgical handpiece. Pressure within the test chamber is lowered prior to removal of the test chamber.

23 Claims, 2 Drawing Sheets

REDUCTION OR ELIMINATION OF THE INTRODUCTION OF AIR WITHIN FLUID INTRODUCED INTO A SURGICAL FIELD

BACKGROUND OF THE INVENTION

1. Field of the Invention

The present invention relates to reducing or eliminating the inflow of air into a surgical field that occurs during the time that a surgical instrument is used to introduce fluid into the surgical field.

2. Discussion of Related Art

Alcon Laboratories commercializes the SERIES 2000® LEGACY® phacoemulsifier, which is advertised on its website at www.alconlabs.com. The phacoemulsifier includes a console for the physician or medical technician to operate that is programmed to control the operation cation surgical handpiece by sending appropriate command signals. The applicant is featured on the website with respect to advice that the applicant provides for use with the phacoemulsification surgical handpieces to physicians who use the phacoemulsifier in their medical practice. With respect to infusion, some of the advice found on the website that the applicant provides for the benefit of physicians includes the following:

Although gravity infusion has historically been the standard method for delivering fluid to the eye during phaco, problems with reliability and efficiency exist. These are:

1. Variable infusion rate depending upon fluid volume within the infusion bottle, Fluid cannot leave the infusion bottle unless it is replaced by air, and this is more difficult when the bottle is relatively full. This is so because the air must travel upward through the entire fluid space, which offers resistance to this exchange. In summary, fluid flows from the bottle with somewhat greater difficulty at the beginning of a procedure than it does at the end of the procedure.

2. The ease with which air enters the infusion bottle is dependent upon the resistance within the "spike vent". This vent has an air filter and in most designs a check valve to prevent liquid leakage. Both of these offer variable resistance to air flow which is in turn manifest as a variation in infusion capacity and resulting perioperative Iop.

Gravity infusion is not the only method by which infusion can be delivered to the eye during phacoemulsification or vitreoretinal procedures. The GFI® system, currently available with the ALCON® ACCURUS® phacoemulsification and/or vitrectomy system, delivers infusion by maintaining pressure within an infusion source that does not require elevation above the patient's eye level. Infusion flow is delivered more precisely and accurately with such a system, and this permits the surgeon to maintain absolute control over chamber depth with the simple press of a button.

Two brief preparatory steps should be made before insertion of a phaco tip of a phaco-emulsification handpiece.

With the test chamber in place on the tip, hold the handpiece vertically with the tip aimed at the ceiling. Depress the footpedal into position 3 for 2 seconds. This will remove air which may have remained in the handpiece during preparation, and eliminate the sudden shower of air bubbles into the anterior chamber at the beginning of the procedure.

Check to be certain that the infusion line is securely inserted into the handpiece. Then remove the teat chamber and depress the footpedal into position 1 to verify that infusion flow is both present and appropriate in degree. The handpiece is now ready for use.

Adequate infusion capacity must be maintained by infusion bottle elevation; a drip chamber level of at least 40 inches (100 cm) above the eye should be present.

After achieving nuclear segmentation (or nucleus flipping for those who prefer this technique), set the flow rate at 40–60 cc/mm and 500 mmHg vacuum with the KELMAN Flared MACKOOL ABS tip.

As always, place a second instrument (spatula or chopper) behind the last nucleus segments to be removed in order to protect the posterior capsule in the event of an infusion misdirection syndrome.

U.S. Pat. No. 5,213,669 ('669 patent), whose contents are incorporated by reference, recognized the risk of thermal injury to the anterior segment of the eye during the use of phacoemulsification. The '669 patent recognized that the implosion of microbubbles during the process generate massive fluid and shock waves that erode the solid material cataractous nuclei, and can release excess thermal energy into the eye. To prevent heat damage, the '669 patent recommended that a constant flow of balanced salt solution in and out of the anterior segment be provided to transfer heat out of the eye and to remove lens debris (lens milk) so that the surgeon can visualize the area. However, any problem with proper balanced salt solution circulation can quickly result in heat damage to eye tissue. To insure proper circulation, the '669 patent recommended that the surgeon should personally perform, among others, the following two steps:

1. Visually be certain that balanced salt solution is being aspirated from the transparent test chamber into the catchment device, that the test chamber remains filled or only slightly dimpled when the device is in phaco mode and held at eye level, and that balanced salt solution exits from the silicone infusion ports before the device is placed in the anterior chamber;

2. Kink the infusion line while in phaco mode and watch for the test chamber to collapse. Follow this by kinking the aspiration line and listen for the sound of vacuum build up.

The present applicant observes that the introduction of air bubbles into the eye is very common during the ultrasonic procedure known as phacoemulsification, and also during non-ultrasonic removal of lens material by irrigation and aspiration. The applicant has performed tens of thousands of phacoemulsification and irrigation/aspiration procedures, and has been able to identify the source of the problem which is as follows.

After preparation of the handpiece for insertion into the eye, air enters the distal portion of the handpiece from the atmosphere either 1) immediately upon the removal of the "test chamber" (a malleable chamber that surrounds the tip of the handpiece and isolates it from the atmosphere), or 2) as the tip is lowered toward the eye and fluid passively drains from the infusion channels in the distal portion of the handpiece and is replaced by atmospheric air. The air travels to the highest portion of the infusion channel to which it can gain access, and remains there until such time during the surgical procedure when it is carried into the eye by infusion fluid. This may occur early in the procedure, but it can be delayed if relatively low infusion flow does not create enough force on the air bubble to pull it away from its tenuous attraction to the inner wall of the infusion channel. It would be desirable to prevent air from entering into the handpiece in the first place, and thereby eliminate the problem.

Although the problem could be eliminated by the maintenance of constant flow of infusion after preparation of the handpiece and beginning immediately with removal of the above described test chamber, this creates the problem of wide dispersion of fluid onto the surgical field as the handpiece approaches the eye. Such dispersion occurs because the usual pressure head within the infusion system (40–90 mm Hg) drives infusion fluid forcefully from the handpiece. This often causes the surgeon to have poor visibility of the surgical organ, or causes the patient to be startled by the sudden rush of fluid onto the portion of the body to be operated upon. Furthermore, the ultrasonic instrument is prepared with a test chamber in place, and even if infusion is activated prior to removal of the test chamber, there is a sudden escape of the pressurized fluid into the atmosphere when the test chamber is removed, and air is therefore still able to gain access into the distal infusion channel as a replacement to the exit of the pressurized infusion fluid.

SUMMARY OF THE INVENTION

The introduction of air into an infusion line may be reduced or eliminated by lowering the pressure of either an infusion fluid or of a test chamber that encloses the needle to a predetermined level. The test chamber pressure may be lowered by occluding the infusion line and activating the aspiration pump. Thereafter, the infusion line may be partially occluded or fully opened and then the test chamber may be removed to permit a constant, low flow rate of infusion through a surgical handpiece.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE DRAWING

Figure 1:
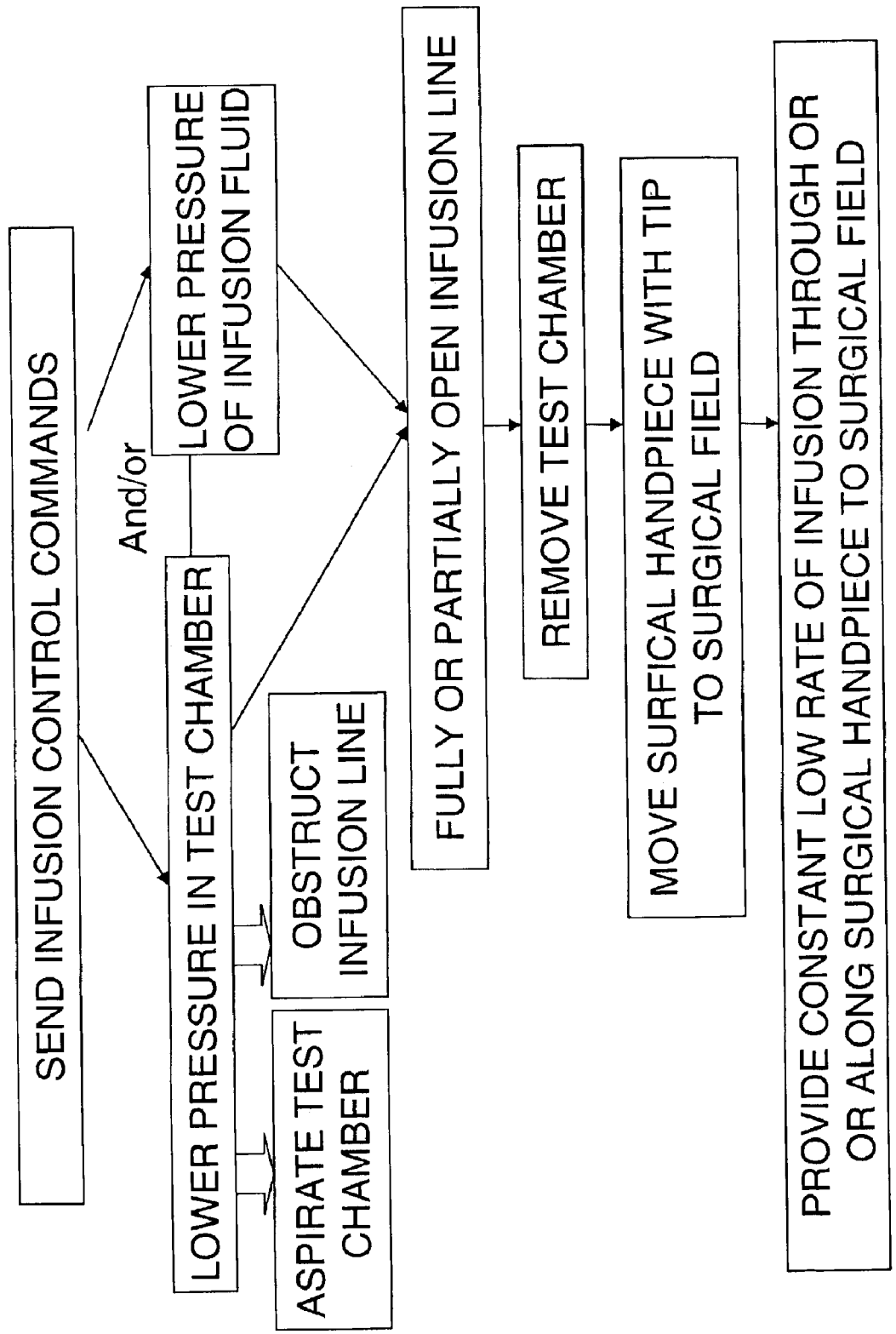
FIG. 1 is a schematic representation of a sequence of steps for carrying out the invention.
Figure 2:
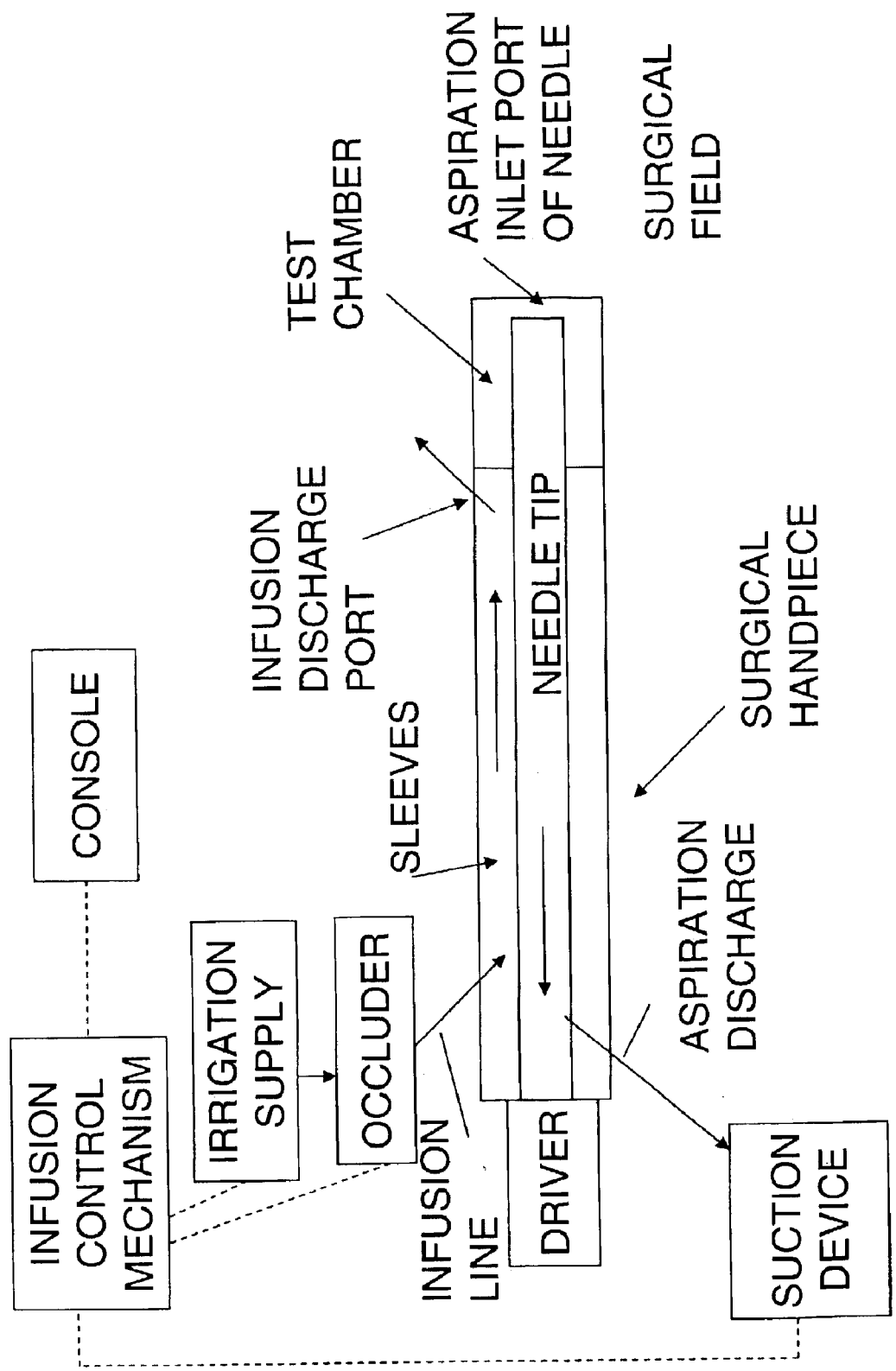
FIG. 2 is a schematic representation of the equipment used for carrying out the sequence of FIG. 1.

Turning to the drawing, FIG. 1 illustrates the recommended sequence of steps and FIG. 2 illustrates the equipment used.

To eliminate the problem of the introduction of air bubbles, the console can be activated to "prepare the handpiece for insertion" by automatically sending a signal to the infusion control mechanism to issue commands (and serve as a means for generating commands) to appropriate drivers (that serve as means responsive to the commands) to lower the pressure within the test chamber to a predetermined level and/or to reduce the infusion pressure. The drivers may be part of an irrigation supply or an occluder to open or close the infusion line and partially or substantially occlude the infusion line.

Whether the test chamber pressure is lowered or the infusion pressure is reduced, the infusion line may then be partially or fully opened prior to removal of the test chamber to provide a constant low rate of infusion through the surgical handpiece. Lowering the pressure within the test chamber may be effected by a) partially opening (or partially occluding) the infusion line and b) activating the aspiration pump to aspirate the test chamber. Note that the order of action a and b can be reversed or occur simultaneously. Also, when first activating the infusion control mechanism, it may be necessary to automatically lower the pressure in the test chamber by momentarily aspirating fluid from the test chamber while obstructing infusion, then partially opening (or partially occluding) the infusion line or channel prior to removal of the test chamber.

The infusion pressure may be reduced by the action of an appropriate driver to reduce infusion pressure, such as by either reducing the height of the infusion fluid supply (gravitational infusion supply as a means for reducing an elevational level of the infusion supply to the infusion line) or decreasing the pressure within the infusion supply (pressurized infusion supply as a means for decreasing a pressure within the infusion supply to the infusion line). Preferably, the infusion pressure is lowered to a level less than the 40–90 mmHg pressure head within the infusion line. The result of this action Is to create a constant low rate of infusion when the test chamber is subsequently removed. This constant dripping of infusion fluid does riot permit air to enter the infusion line, e.g., the distal infusion pathway.

The handpiece (including the tip) are then moved into the surgical field and the tip is introduced into the organ. Immediately thereafter, the surgeon may activate the console to a previously programmed state whereby the partial occlusion line obstruction is eliminated, a greater infusion pressure head is present (as a means for providing a rate of flow of infusion fluid), and footpedal depression by the surgeon would result in activation of a pump of a suction device, with tissue removal, tip vibration or oscillation, etc.

The infusion line or channel may irrigate the surgical field with a balanced salt solution, saline solution or the like. The needle tip is vibrated or oscillated by a driver. The tissue removal arises by sucking the tissue through the aspiration inlet port through the tip and needle to pass through the aspiration discharge to the suction device.

The needle may or may not have one or more exterior sleeves that extend along its length up to the proximal portion of the tip. Irrigation fluid may flow along the exterior surface of the needle or, if two concentrically arranged sleeves are provided, through passage between the sleeves.

While the foregoing description and drawings represent the preferred embodiments of the present invention, it will be understood that various changes and modifications may be made without departing from the spirit and scope of the present invention.

What is claimed is:

1. A method to reduce air introduction via infusion through a surgical handpiece, comprising generating commands;

in response to the commands, lowering a pressure within a test chamber by reducing pressure of an infusion fluid;

removing the test chamber from the surgical handpiece; and providing a rate of flow of the infusion fluid through an infusion line as a consequence of the lowering of the pressure upon removal of the test chamber from the surgical handpiece.

2. A method as in claim 1, wherein the lowering of the pressure includes reducing an elevation level of an infusion supply to the infusion line.

3. A method as in claim 1, wherein the lowering of the pressure includes decreasing a pressure within an infusion supply to the infusion line, the infusion line extending along the surgical handpiece.

4. A method to reduce air introduction via infusion through a surgical handpiece, comprising generating commands;

in response to the commands, lowering a pressure within a test chamber by momentarily aspirating fluid from the teat chamber while obstructing an infusion line and then partially opening the infusion line;

thereafter removing the test chamber from the surgical handpiece; and providing a rate of flow of infusion fluid through the infusion line as a consequence of the lowering of the pressure upon removal of the test chamber from the surgical handpiece.

5. A method as in claim 4, wherein the aspirating and the obstructing occur simultaneously.

6. A method as in claim 4, wherein the aspirating and the obstructing occur one after the other.

7. A method to reduce air introduction via infusion through a surgical handpiece, comprising generating commands;

in response to the commands, lowering a pressure within a test chamber by partially removing an obstruction in an infusion line so that the obstruction at most substantially, yet not fully, occludes the infusion line and thus partially opens the infusion line;

removing the test chamber from the surgical handpiece; and providing a rate of flow of infusion fluid as a consequence of the lowering of the pressure upon removal of the test chamber from the surgical handpiece.

8. A method as in claim 7, wherein the lowering of the pressure includes reducing an elevation level of an infusion supply to the infusion line.

9. A method as in claim 7, wherein the lowering of the pressure includes decreasing a pressure within an infusion supply to the infusion line.

10. A method as in claim 7, further comprising removing the obstruction from the infusion line to increase an infusion pressure head, and irrigating through the infusion line with the increased infusion pressure head, and vibrating or oscillating a needle of the surgical handpiece while carrying out the irrigating.

11. A method as in claim 10, further comprising removing tissue with the surgical handpiece while carrying out the irrigating.

12. An apparatus to reduce air introduction via infusion through a surgical handpiece, comprising means for generating commands; means responsive to the commands for lowering a pressure with a test chamber and means for providing a rate of flow of infusion fluid through an infusion line upon removal of the test chamber from the surgical handpiece as a consequence of the lowering of the pressure by said means responsive to the commands for lowering a pressure, the means responsive to the commands for lowering of the pressure includes means for reducing pressure of the infusion fluid.

13. An apparatus as in claim 12, wherein the means for reducing includes means for reducing an elevation level of an infusion supply to the infusion line.

14. An apparatus as in claim 12, wherein the means for reducing includes means for decreasing a pressure within an infusion supply to the infusion line.

15. An apparatus as in claim 12, further comprising means for removing tissue fragments with the surgical handpiece by suction.

16. An apparatus to reduce air introduction via infusion through a surgical handpiece, comprising means for generating commands; means responsive to the commands for lowering a pressure within a test chamber and means for providing a rate of flow of infusion fluid through an infusion line upon removal of the test chamber from the surgical handpiece as a consequence of the lowering of the pressure by said means responsive to the commands for lowering a pressure, the means responsive to the commands for lowering the pressure including means for partially opening the infusion line by partially removing an obstruction in the infusion line so that the obstruction at most substantially, yet not fully, occludes the infusion line with the obstruction.

17. An apparatus as in claim 16, wherein the means for lowering includes means responsive to the commands for reducing an elevation level of an infusion supply to the infusion line.

18. An apparatus as in claim 16, wherein the means responsive to the commands for lowering includes means for decreasing a pressure within an infusion supply to the infusion line.

19. An apparatus as in claim 16, further comprising means for increasing infusion pressure head by removal of the obstruction from the infusion line.

20. An apparatus as in claim 19, further comprising means for irrigating through the infusion line with the increased infusion pressure head, and means for vibrating or oscillating a needle of the surgical handpiece while the means for irrigating is effecting the irrigating through the infusion line.

21. An apparatus to reduce air introduction via infusion through a surgical handpiece, comprising means for generating commands; means responsive to the commands for lowering a pressure within a test chamber and means for providing a rate of flow of the infusion fluid through an infusion line upon removal of the test chamber from the surgical handpiece as a consequence of the lowering of the pressure by said means responsive to the commands for lowering a pressure, the means responsive to the commands for lowering pressure including means for reducing pressure in the test chamber by momentarily aspirating fluid from the test chamber while obstructing the infusion line with the obstruction and then partially opening the infusion line prior to removal of the test chamber.

22. An apparatus as in claim 21, wherein the means for reducing pressure in the test chamber is configured so that the aspirating and the obstructing occur simultaneously.

23. An apparatus as in claim 21, wherein the means for reducing pressure in the test chamber is configured so that the aspirating and the obstructing occur one after the other.

* * * * *